US00PP24126P2

(12) United States Plant Patent
Stemkens

(10) Patent No.: US PP24,126 P2
(45) Date of Patent: Dec. 31, 2013

(54) ***VERBENA* PLANT NAMED 'VEAZ0015'**

(50) Latin Name: *Verbena hybrida*
Varietal Denomination: VEAZ0015

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 13/573,152

(22) Filed: Aug. 27, 2012

(51) Int. Cl.
*A01H 5/00* (2006.01)

(52) U.S. Cl.
USPC ..... Plt./308

(58) Field of Classification Search
USPC ..... Plt./308
See application file for complete search history.

*Primary Examiner* — Kent L Bell
(74) *Attorney, Agent, or Firm* — Joshua L. Price

(57) ABSTRACT

A new *Verbena* plant named 'VEAZ0015' particularly distinguished by the white and red bi-colored, single to semi double inflorescences, medium green foliage, and an outwardly spreading plant habit.

1 Drawing Sheet

Latin name of the genus and species of the plant claimed: *Verbena hybrida.*

Varietal denomination: 'VEAZ0015'.

BACKGROUND OF THE NEW PLANT

The present invention comprises a new *Verbena*, botanically known as *Verbena hybrida*, and hereinafter referred to by the variety name 'VEAZ0015'.

'VEAZ0015' is a product of a planned breeding program. The new cultivar has white and red bi-colored, single to semi double inflorescences, medium green foliage, and an outwardly spreading plant habit.

'VEAZ0015' originated from an open-pollinated hybridization made in August 2007 in a greenhouse in Enkhuizen, The Netherlands. The female parent was an unpatented proprietary plant designated 'KO515-2' with single rose with a white eye floret color and a smaller floret size.

The male parent of 'VEAZ0015' was unknown. The seed was sown in February 2008 in a greenhouse in Enkhuizen, The Netherlands. 'VEAZ0015' was selected as one flowering plant within the progeny of the stated open pollination in the August 2008.

The first act of asexual reproduction of 'VEAZ0015' was accomplished when vegetative cuttings were propagated from the initial selection in August 2008 in a greenhouse in Enkhuizen, The Netherlands.

BRIEF SUMMARY OF INVENTION

Horticultural examination of plants grown from cuttings of the plant initiated in August 2008, and continuing thereafter, has demonstrated that the combination of characteristics as herein disclosed for 'VEAZ0015' are firmly fixed and are retained through successive generations of asexual reproduction.

'VEAZ0015' has not been observed under all possible environmental conditions. The phenotype may vary significantly with variations in environment such as temperature, light intensity, and day length.

Plant Breeder's Rights for this cultivar were applied for in Canada on Nov. 1, 2011(11-7419) and in the Community Plant Variety Office on Oct. 28, 2011(2011/2556). 'VEAZ0015' has not been made publicly available more than one year prior to the filing of this application.

The following traits have been repeatedly observed and are determined to be basic characteristics of the new variety. The combination of these characteristics distinguishes this *Verbena* as a new and distinct variety.

BRIEF DESCRIPTION OF THE PHOTOGRAPHS

The accompanying photographic drawings show typical flower and foliage characteristics of 'VEAZ0015' with colors being as true as possible with illustrations of this type.

Figure 1:
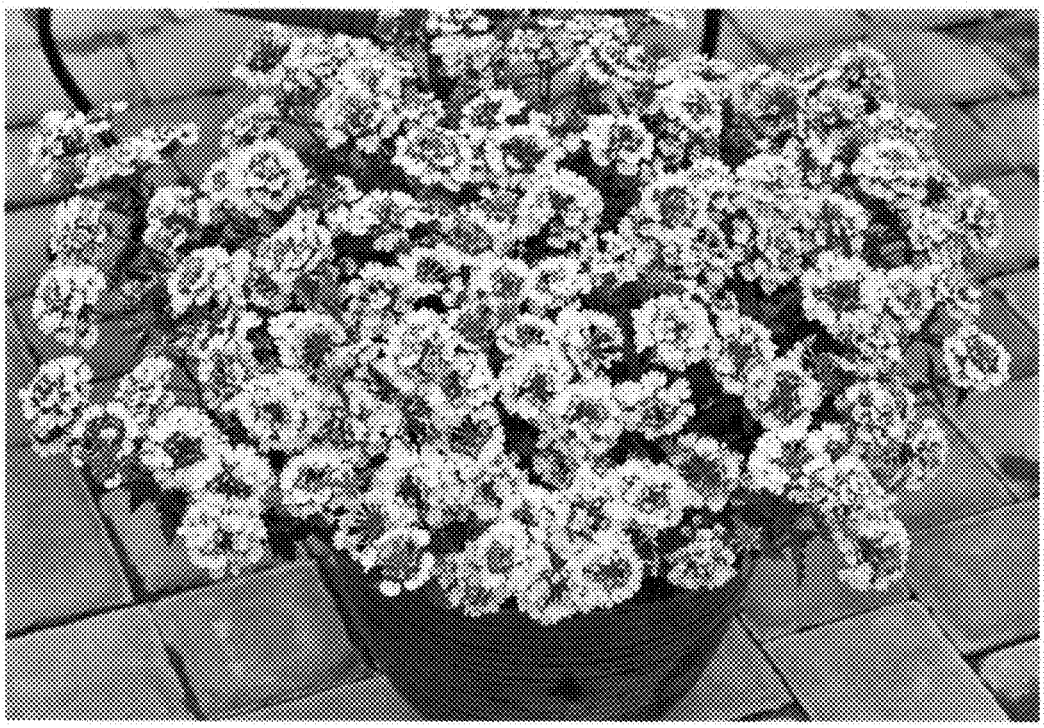
Figure 2:
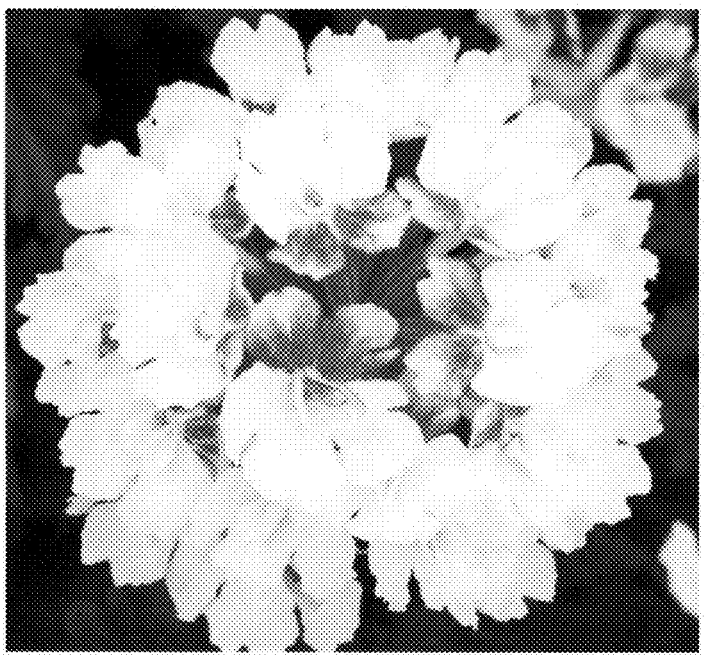

The photographic drawing in FIG. 1 shows four flowering plants of the new variety, and in FIG. 2 a close-up of the inflorescence.

DETAILED BOTANICAL DESCRIPTION

The plant descriptions and measurements were taken in Enkhuizen, The Netherlands in early August 2012 in outdoor natural light. The plants used were about 20 weeks of age, growing in 30 cm wide×1 meter long window boxes, outside in full sun.

The aforementioned photographs were taken in March 2012 in Gilroy, Calif. in a greenhouse. These plants were approximately 15 weeks of age growing in a 14 inch container, in a greenhouse.

Color references are made to The Royal Horticultural Society Colour Chart (R.H.S.) 2001.

TABLE 1

DIFFERENCES BETWEEN THE NEW VARIETY 'VEAZ0015' AND A MOST SIMILAR VARIETY

| | 'VEAZ0015' | 'Flagdena' (U.S. Plant Pat. No. 22,438) |
|---|---|---|
| Floret type: | Single to Semi-double | Single |
| Floret base color: | More yellow-green | More pure white |
| Floret upper petals | More mottled | More solid |

TABLE 1-continued

DIFFERENCES BETWEEN THE NEW VARIETY 'VEAZ0015' AND A MOST SIMILAR VARIETY

| | 'VEAZ0015' | 'Flagdena' (U.S. Plant Pat. No. 22,438) |
|---|---|---|
| 2nd color pattern: | | |
| Floret upper petals | More red | More red-purple |
| 2nd color: | | |
| Floret shape: | Slightly cupped | Very flat |

Plant:

*Form, growth and habit.*—Herbaceous, initially mounding then outwardly spreading; vigorous and free-branching.

*Plant height.*—12.0 cm.

*Plant height* (*inflorescence included*).—22.0 cm.

*Plant width.*—50.0 cm.

Roots:

*Number of days to initiate and produce roots.*—11-14 days at about 22 degrees C.

*Type.*—Fine, fibrous, free branching.

*Color.*—RHS N155B but whiter.

Foliage:

*Arrangement.*—Opposite, simple.

*Immature, leaf color, upper surface.*—RHS 137B.

*Immature, leaf color, lower surface.*—RHS 138B.

*Mature, leaf color, upper surface.*—RHS 137B.

*Mature, leaf color, lower surface.*—RHS 138B.

*Length.*—5.0 cm.

*Width.*—1.5 cm.

*Shape.*—Ovate.

*Base shape.*—Attenuate.

*Apex shape.*—Apiculate.

*Margin.*—Dentate.

*Texture, upper surface.*—Pubescent.

*Lower surface.*—Pubescent; glandular hairs.

*Color of veins, upper surface.*—RHS 145B.

*Color of veins, lower surface.*—RHS 145B.

*Pattern of veining.*—Pinnate.

*Petioles color.*—RHS 145B.

*Petioles length.*—0.5 cm.

*Petiole width.*—0.3 cm.

*Texture.*—Hirsute; glandular hairs.

Stem:

*Quantity of main branches per plant.*—About 11.

*Color of stem.*—RHS 144A.

*Stem length.*—About 25.0 cm.

*Stem width.*—About 0.5 cm.

*Length of internodes.*—4.5-6.5 cm.

*Texture.*—Pubescent.

*Color of peduncle.*—RHS 144B.

*Length of peduncle.*—5.0 cm.

*Peduncle diameter.*—0.2 cm.

*Texture.*—Pubescent.

Inflorescence:

*Type.*—Umbel-like, but actually a spike, umbrella-shaped to semi spherical.

*Blooming habit.*—Flowers continuously.

*Lastingness of individual blooms on the plant.*—About 6-10 days in the greenhouse.

*Fragrance.*—Slight.

*Number of inflorescences per plant.*—46 at various stages.

*Horizontal diameter of inflorescence.*—About 5.5 cm.

*Depth of inflorescence.*—2.5 cm.

*Number of florets per inflorescence* (*including any buds at the time*).—20.

Bud (just when opening/showing color):

*Color.*—RHS 1D with blushes of RHS 55D.

*Length.*—0.8 cm.

*Width.*—0.9 cm.

*Shape.*—Tubular with bulbous apex.

Corolla:

*Form.*—Sessile; salverform, composed of 5 partly fused petals with a base of a narrow tube, and sometimes a semi-double composed of 6-7 petals and petaloids.

*Immature color,* 2 *top petals, upper surface.*—Closest to RHS 150C overlaid with blushes and hues of RHS 53B.

*Immature color,* 2 *top petals, lower surface.*—RHS 155D with some blushes of RHS 56D on the margins.

*Immature color,* 3 *lower petals, upper surface.*—Closest to RHS 145C to RHS 145D.

*Immature color,* 3 *lower petals, lower surface.*—Closest to RHS 150D with a little blush of RHS 145C.

*Mature color,* 2 *top petals, upper surface.*—RHS 154D overlaid with blushes and hues of RHS 53B to RHS 53C.

*Mature color:* 2 *top petals, lower surface.*—RHS 155D overlaid with blushes of RHS 56C.

*Mature color,* 3 *lower petals, upper surface.*—RHS 150D.

*Mature color,* 3 *lower petals, lower surface.*—RHS 150D with a little blush of RHS 145C.

*Floret diameter.*—1.5 cm.

*Floret length* (*depth*).—2.0 cm.

*Petal length.*—0.7 cm.

*Petal width.*—0.6 cm.

*Shape.*—Orbicular.

*Apex shape.*—Emarginate.

*Margin.*—Entire.

*Petal texture, upper surface.*—Papillose; few glandular hairs.

*Petal texture, lower surface.*—Papillose, pubescent, some glandular hairs.

*Quantity of petaloids.*—2-3; sometimes the petaloids are folded and not laying out flat.

*Color of petaloids.*—Colors are relative to the regular petals but based on the proximity to the type of regular petal (top or lower).

*Petaloid length.*—0.5 cm.

*Petaloid width.*—0.1-0.5 cm.

*Petaloid shape.*—Orbicular.

*Petaloid apex shape.*—Emarginate.

*Petaloid margin.*—Entire.

*Petaloid texture, upper surface.*—Papillose; few glandular hairs.

*Petaloid texture, lower surface.*—Papillose ; pubescent, some glandular hairs.

*Corolla tube length.*—2.6 cm.

*Corolla tube width.*—0.2 cm.

*Corolla tube color inside.*—RHS 150D.

*Tube color outside.*—RHS 150C.

*Corolla texture, inside.*—Papillose.

*Corolla texture, outside.*—Hirsute.

*Throat hair color.*—RHS 155D but whiter.

Calyx:

*Type.*—Five sepals whose margins are fused to each other along their length, with a transparent membrane of less than 0.1 cm in width and with one smaller sepal attached to the base of the calyx.

*Color of sepals.*—RHS 138B, with anthocyanins at the apex of about RHS 187B.

*Length of sepals.*—1.1 cm.

*Width of sepals.*—0.2 cm.

*Sepal shape.*—Linear.

*Apex shape.*—Apiculate.

*Margins.*—Entire.

*Texture.*—Velutinous; glandular hairs.

Reproductive organs:

*Gynoecium.*—Pistil: 1. Pistil length: 1.5 cm. Style color: RHS N144D. Style length: 1.4 cm. Stigma color: RHS 141C. Ovary color: RHS 144B. Ovary length: 0.2 cm. Ovary width: 0.1 cm.

*Androecium.*—Stamens: Anthers and filaments fused to upper half of corolla tube; four anthers with two pollen sacs per anther. Color of filaments: RHS 154D. Filament length: 0.2 cm. Anther color: RHS 154C. Anther length: 0.1 cm. Pollen amount: None seen to date.

Fertility/seed set: Has not been determined to date.

Disease/pest resistance: Has not been determined to date.

What is claimed is:

1. A new and distinct variety of *Verbena* plant named 'VEAZ0015' substantially as illustrated and described herein.

* * * * *